United States Patent
Procter

(10) Patent No.: US 8,814,920 B2
(45) Date of Patent: Aug. 26, 2014

(54) IMPLANTATION DEVICE, METHOD FOR PRODUCING AND FOR APPLYING THE SAME

(75) Inventor: Philip Procter, Geneva (CH)

(73) Assignee: Stryker Trauma GmbH (DE)

( * ) Notice: Subject to any disclaimer, the term of this patent is extended or adjusted under 35 U.S.C. 154(b) by 490 days.

(21) Appl. No.: 12/532,549

(22) PCT Filed: Mar. 19, 2008

(86) PCT No.: PCT/EP2008/002220
§ 371 (c)(1),
(2), (4) Date: Sep. 22, 2009

(87) PCT Pub. No.: WO2008/116591
PCT Pub. Date: Oct. 2, 2008

(65) Prior Publication Data
US 2010/0036441 A1    Feb. 11, 2010

(30) Foreign Application Priority Data
Mar. 23, 2007   (EP) ..................................... 07006080

(51) Int. Cl.
| | | |
|---|---|---|
| A61B 17/04 | (2006.01) | |
| A61B 17/84 | (2006.01) | |
| A61F 2/08 | (2006.01) | |
| A61B 17/86 | (2006.01) | |
| A61B 17/56 | (2006.01) | |
| A61B 17/58 | (2006.01) | |
| A61F 2/30 | (2006.01) | |

(52) U.S. Cl.
USPC ............................ 606/331; 606/329; 606/76

(58) Field of Classification Search
USPC .......... 606/70, 76–79, 280, 329, 331; 600/585
See application file for complete search history.

(56) References Cited

U.S. PATENT DOCUMENTS

| | | | |
|---|---|---|---|
| 4,344,190 A * | 8/1982 | Lee et al. .......................... 606/95 |
| 6,548,569 B1 | 4/2003 | Williams et al. | |
| 8,202,306 B2 * | 6/2012 | Dreyfuss ........................ 606/329 |
| 2004/0030341 A1* | 2/2004 | Aeschlimann et al. .......... 606/72 |
| 2005/0182411 A1* | 8/2005 | DeMeo et al. ................... 606/77 |
| 2005/0249773 A1* | 11/2005 | Maspero et al. ............... 424/423 |
| 2006/0188546 A1* | 8/2006 | Giroux .......................... 424/426 |

FOREIGN PATENT DOCUMENTS

| | | |
|---|---|---|
| EP | 1609494 A1 | 12/2005 |
| WO | 9846164 A1 | 10/1998 |

OTHER PUBLICATIONS

International Search Repoet and Written Opinon, PCT/EP2008/002220, dated Oct. 8, 2008.

* cited by examiner

*Primary Examiner* — Andrew Yang
*Assistant Examiner* — Diana S Jones
(74) *Attorney, Agent, or Firm* — Lerner, David, Littenberg, Krumholz & Mentlik, LLP

(57) ABSTRACT

An implantation device for fixating a bone has a main body. The main body has a peripheral region and comprises a polymeric material. The peripheral region comprises the polymeric material and a plasticizer. In particular, the peripheral region may be adapted to be fixed to a bone. A method for producing the implantation device includes the steps of forming an implantation device using polymer material, and dipping at least a portion of the implantation device into a plasticizer in such a way that a peripheral region of the implantation device is plasticized.

14 Claims, 6 Drawing Sheets

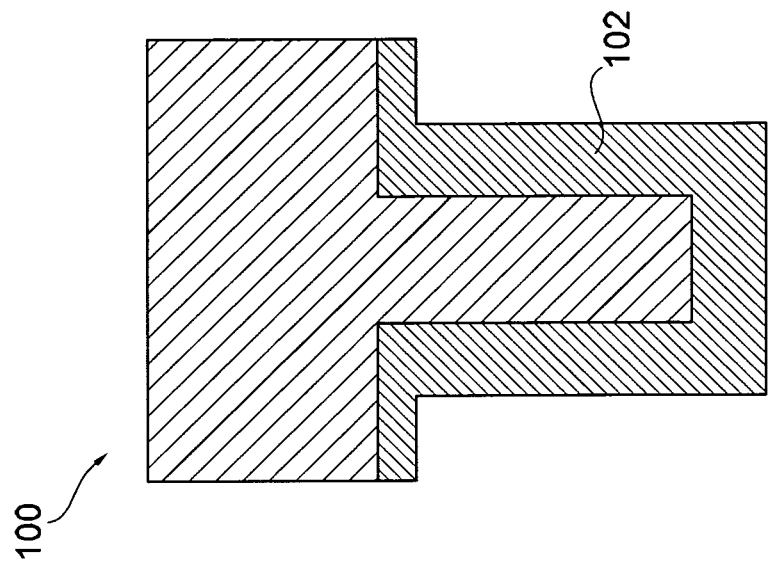
Fig. 1B
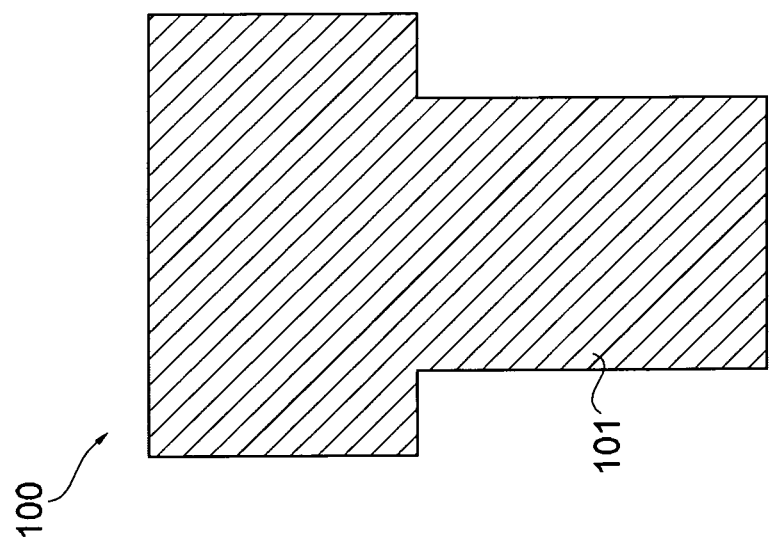
Fig. 1A
Fig. 1

IMPLANTATION DEVICE, METHOD FOR PRODUCING AND FOR APPLYING THE SAME

CROSS REFERENCE TO RELATED APPLICATIONS

The present application is a national phase entry under 35 U.S.C. §371 of International Application No. PCT/EP2008/002220, filed Mar. 19, 2008, published in English, which claims the benefit of European Patent Application No. 07 006 080.1, filed Mar. 23, 2007. The disclosures of said applications are incorporated by reference herein.

FIELD OF INVENTION

The invention relates to an implantation device, a method for producing and for applying the same, in particular a bone pin which is implementable without the application of sonic energy.

TECHNICAL BACKGROUND

The invention relates to implants for humans or animals. The implants at least partly create positive-fit connections to human or animal tissue parts, particularly skeletal parts, wherein the implants help connect tissue parts together, or help connect tissue parts to means supporting or replacing tissue parts, or to other therapeutic auxiliary devices. The invention further relates to methods for implanting implants into humans or animals.

Known implants for creating connections to skeletal parts (bones) include screws, pins, etc., which are used for connecting bones to bones, or bones to artificial, carrying, stabilizing, or supporting parts, or to parts replacing skeletal parts (stabilization or fixation plates, sutures, wires, artificial joint elements, artificial teeth, etc.). Such connection elements for implantation consist for example of metal or plastic, including resorbable plastic. After healing, the connection elements are removed by a further operation or they are left in the body where they are possibly gradually decomposed and replaced by vital tissue.

For stabilizing a bone fracture, a fixation plate with suitable holes is fixed in the region of the fracture using screws as mentioned above. Plate and screws may consist of metal (e.g. stainless steel or titanium). The screws are self-cutting and are rotated into threadless openings in the bone, or they are screwed into pre-drilled threaded openings. Pins are inserted into previously created openings for similar purposes. Connections created in the foregoing manner are usually based on frictional engagement, possibly on positive fit.

It is known also to use curable, plastic materials (e.g. particular cements on a hydraulic or polymer base) for creating connections of the mentioned type. Such materials are pressed from the outside between implant and vital tissue, or into tissue defects in a highly viscous condition, and are cured in situ. Positive-fit connections can be created using such material, if the openings into which the material is pressed comprise suitable undercuts. In order to reduce the stress and/or costs of the corresponding operation method so-called biodegradable implants, e.g. bone pins are used. That is, bone pins which degrade over time and which are then absorbed by the body. One of such known biodegradable bone pins is known under the trademark Polypin. This bone pin consists of a polyactid-copolymer mixture and is absorbed during a period of about two years. The attachment of such resorbable polymer pins to bone is done by press fitting such pins into a predrilled hole in a bone.

Also known in the art is the usage of thermoplastic polymer materials which can be liquefied in a targeted manner by way of mechanical oscillation and, in this condition, can be pressed into cavities by way of hydrostatic pressure, thereby creating positive fit connections after solidification.

Furthermore, from U.S.2005/0249773 the importance of bone replacement materials is known, in particular in the areas of orthopedics, traumatology, cranial, dental and facial surgery, and orthodontics continues to increase. Significant areas of application for bone implants include, for example, the closing of large bone defects associated with comminuted fractures as well as the attachment of small bone fragments, the filling of bone defects resulting from bone cysts and after removal of bone tumors, the filling of voids caused by chronic osteomyelitis, applications associated with material loss on alveolis and jaw bones and the use as a carrier material, for example, for antibiotics, cytostatic, and osteogenic materials.

In most cases, bone defects can be treated by the insertion of bone augmentation materials. Healing is promoted if the implants closely contact the surrounding bone walls. Thus, it is advantageous to be able to form a bone implant in a particular shape. For instance, if a tooth is extracted, the bone implant used to fill the void preferably nearly replicates the tooth root. Improperly shaped bone implants can lead to problems such as soft tissue ingrowth and poor adhesion between the implant and existing bone. In addition, improper shape can lead to complications or patient discomfort.

Properly shaping a bone implant is often very challenging. In some cases the repair site is deep within the body and covered by soft tissue and body fluids. In other cases, such as with a tooth extraction, the root of the extracted tooth can be used to make a mold. However, even when repairing a tooth extraction wound, there are times when the root is broken into pieces and not available for molding. In other situations, the bone implant must be molded after it has been placed in the injury site.

According to U.S.2005/0249773 the above-mentioned problems are overcome by providing an osteoconductive and/or osteoinductive biocompatible implant composition that that can be readily molded in-situ or ex-situ into a desired shape. Once the moldable implant composition is formed into a desired shape, the implant composition is easily, and if desired, quickly hardened to form a rigid implant. Such an implant composition may forms an open porous scaffolding or composite matrix that allows in-growth and/or regeneration of bone tissue. In another version, the solvent is included in an amount sufficient to form a liquid implant that can be poured or injected into an implant site.

SUMMARY OF THE INVENTION

There may be a need to provide an implantation device, a method for producing and for applying the same which implantation device may be applicable without the use of mechanical oscillation.

This need may be met by an implantation device, a method for producing and for applying the same according to the independent claims.

According to an exemplary embodiment an implantation device for fixating a bone comprises a main body, wherein the main body has a peripheral region, wherein the main body comprises a polymeric material, and wherein the peripheral region comprises the polymeric material and a plasticizer. In particular, the peripheral region may be adapted to be fixed to a bone.

According to an exemplary embodiment a method for producing an implantation device comprises forming an implantation device using polymer material, and dipping at least a portion of the implantation device into a plasticizer in such a way that a peripheral region of the implantation device is plasticised.

According to an exemplary embodiment a method for applying an implantation device to a target structure, comprises fixating an implantation device according an exemplary embodiment at a target structure in such a way that target structure fragments are fixed to each other by the implantation device.

According to the present invention the term plasticizer may relate to a material, preferably liquid, which has the effect on a polymeric that it softens the polymeric material or has the effect on the polymeric material that the polymer material becomes plastic, i.e. easily formable, or ductile.

An exemplary aspect of an exemplary embodiment of the invention may be seen in that, an implantation device made of polymeric material is dipped into a so-called plasticizer which is used as a surface plasticizer, i.e. only an outer surface region of the implantation device, e.g. a bone pin, dipped into the plasticizer is softened and made sticky, while a core of the implantation device remains solid. This implantation device, having a softened outer surface may then be introduced into a target structure, e.g. a bone, to fix or attach fragments to the bone. Such an implantation device may be easily introducible into a hole drilled into the target area or attached on the outside of bone fragments due to the fact that the implantation device has a soft outer surface. In case the soft outer surface is hardened afterwards, i.e. after the implantation device is inserted into or attached to the bone, the fixation of the bone fragments may be durable and stable. Thus, disadvantages of known bone pins, e.g. that such known pins can become loose and lose their holding power to hold bone fragments together, may be overcome in case an implantation device according to an exemplary embodiment of the present invention is used. Furthermore, since the implantation device prior to insertion into the target structure has already a soft outer surface the use of a material which is liquefiable by sonic energy may be unnecessary. Thus, the implantation process may become simpler, faster and less expensive. According to this aspect the effect of softening a polymer material is used to fix an implant device or a bone pin to the bone, rather than to cause implantable granulate balls to stick together.

Since, the implantation device comprises a softened outer layer which becomes solid again due to the interaction with body fluids no sonic fusion may be required to achieve a stable connection between the implantation device and the bone. Thus, it may be possible to reduce the sound and thermal impact on bone and tissue. Further, the whole process may be performed at body temperature. Furthermore, no taping of the introduced implantation device may be necessary as it is usually in the case of conventional screws.

In the following, further exemplary embodiments of the implantation device will be described. However, these embodiments apply also for the method for producing a implantation device and for the method for applying the implantation device.

According to another exemplary embodiment of the implantation device the polymeric material is bioabsorbable. That is, the material may be absorbed by a human or animal body. Preferably, the bioabsorbable material comprises a copolymer comprising between 50% and 90% Poly-L-lactide and between 10% and 50% Poly-D, L-lactide. In particular, the bioabsorbable material may be a copolymer comprising 70 weight % Poly-L-lactide and 30 weigh % Poly-D, L-lactide. Preferably, the bioabsorbable material may be formed as an amorphous material. Alternatively, the implantation device may be formed by non-absorbable materials.

The above described material may be a suitable material for a implantation device, e.g. a bone pin, which material may exhibit a suitable tensile strength of about 60 MPa, and a suitable E-modulus of about 3500 MPa. Furthermore, the above material, i.e. an implantation device comprising the above material, may retain its strength for about a sufficient time when implanted into a human or animal's body. Such a time span may be about 4 to 26 weeks. The described copolymer may have a resorption time of about two to three years in a human or animal body. The material may further exhibit an increase of implant volume up to 200% after 24 month from the implantation in the target structure. Such a material may further be easily to be sterilized by γ-radiation. A suitable energy dose may be between 20 kGy and 30 kGy, in particular below 25 kGy.

By forming the whole implantation device by the bioabsorbable material the use of the implantation device may be simplified. In particular, no additional operation may be necessary to remove the implantation device or parts of it after a healing process of the target structure has been completed.

Additional to the above described material there a plurality of different materials suitable to be used as a material of the implantation device.

A first group of these materials may be biodegradable polymer or copolymer, said polymer or copolymer may be selected from the group consisting of homopolymers or copolymers of polyesters, polyorthoesters, polylactides (PLA), polyglycolides (PGA), polycaprolactones, polyhydroxybutyrates, polyhydroxyvalerates, pseudopolyamino acids, polyamides and polyanhydrides. Suitable plasticizers for the first group of materials may be selected from the group consisting of citrates, phthalates, glycol ethers, n-methylpyrrolidone, 2 pyrrolidone, propylene glycol, glycerol, glyceryl dioleate, ethyl oleate, benzylbenzoate, glycofurol, sorbitol, sucrose acetate isobutyrate, butyryltri-n-hexyl-citrate, acetyl-tri-n-hexyl citrate, sebacates, dipropylene glycol methyl ether acetate (DPM acetate), propylene carbonate, propylene glycol laurate, propylene glycol captylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di and tri stearate, glyceryl palmitostearate, and glyceryl triacetate.

A second group of these materials may be bioerodible synthetic polymers including poly(lactic acid) and polyglycolic acid, or their derivatives; polylactides; polyglycolides; copolymers of lactides and glycolides (PGA/PLA); oligomers of glycolic acid and/or lactic acid and their derivatives with alcohols and/or carbonic acids; polylactide-glycerate; polyglycolide-co-glycerate; polyamides; polyesters; oligomers of hydroxycarbonic acids; poly(ortho)esters; polycaprolactones; polyanhydrides; pyrrolidones (e.g., methylpyrrolidone); and cross-linked cellulosic polymers (e.g., carboxymethyl cellulose). Mixtures and combinations of these may also be used. Suitable plasticizers for the second group of materials may be selected from the group consisting of citrates, phthalates, glycol ethers, n-methylpyrrolidone, 2 pyrrolidone, propylene glycol, glycerol, glyceryl dioleate, ethyl oleate, benzylbenzoate, glycofurol, sorbitol, sucrose acetate isobutyrate, butyryltri-n-hexyl-citrate, acetyltri-n-hexyl citrate, sebacates, dipropylene glycol methyl ether acetate (DPM acetate), propylene carbonate, propylene glycol laurate, propylene glycol captylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di and tri stearate, glyceryl palmitostearate, and glyceryl triacetate.

A third group of these materials may be biodegradable/bioerodible thermoplastic polymer which is selected from the group consisting of polylactides, polyglycolides, polycaprolactones, polyethylene glycols, polyanhydrides, polyamides, polyurethanes, polyesteramides, polyorthoesters, polydioxanones (PDS), polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly methyl vinyl ether), chitin, chitosan, and copolymers, terpolymers, and any combination thereof. Suitable plasticizers for the third group of materials may be selected from a group of organic solvent wherein the group consists of N-methyl-2-pyrrolidone, 2-pyrrolidone, ethanol, propylene glycol, acetone, acetic acid, ethyl acetate, ethyl lactate, methyl acetate, methyl ethyl ketone, dimethylformamide, dimethyl sulfoxide, dimethyl sulfone, tetrahydrofuran, caprolactam, decylmethylsulfoxide, oleic acid, propylene carbonate, N,N-diethyl-m-toluamide, and 1-dodecylazacycloheptan-2-one.

Furthermore, resorbable polymers like polyglycolides (PGA), polylactides (PLA), glycolide/lactide copolymers (PGA/PLA), glycolide/trimethylene carbonate copolymers (PGA/TMC), poly-.beta.-hydroxybutyric acid (PHBA), poly-.beta.-hydroxypropionic acid (PHPA), poly-.beta.-hydroxyvaleric acid (PHVA), PHBA/PHVA copolymers, poly-p-dioxanone (PDS), poly-1,4-dioxanon-2,5-dione, polyesteramides (PEA), poly-.epsilon.-caprolactones, poly-.delta.-valerolactone, poly-carbonate, polyesters of oxalic acid, glycolic esters, and dihydropyranes may be used.

According to another exemplary embodiment of the implantation device the polymeric material is one of the group consisting of polyethylene, in particular of an implantable grade, nylon.

According to another exemplary embodiment of the implantation device the plasticizer is of a material which reacts with a body fluid, in particular it may react with blood. In particular, the implantation device the plasticizer may be N-Methyl Pyrolidone.

By using a plasticizer which reacts with a body fluid, e.g. blood, a surprisingly easy mechanism may be provided by which the softened outer surface of the implantation device may be hardened after the implantation device is introduced into or attached to the target structure, e.g. a bone. That is, the contact of the plasticizer may chemically reverses the softening process of the outer surface of the implantation device, since the plasticizer hardens when it comes into contact with blood. After the plasticizer is leached into the region circumferentially surrounding the bone, the core polymer material, i.e. the original polymeric material the implantation device is made of, may be firmly fixed into the drilled bone hole or firmly fixed at the bone.

According to another exemplary embodiment of the implantation device a core region of the main body is free of plasticizer. That is, in case of a cylindrical implantation device only an outer circumferential region may be softened by the plasticizer, while an inner region or core region of the implantation device may remain hard. Preferably, the softened peripheral region may have a thickness of about 0.1 mm to 2 mm. In particular, the softened peripheral region may have a thickness depending on a size of the implantation device, e.g. for a small implantation device the softened region may have a thickness of about 0.1 mm, for a medium implantation device of about 1 mm and for a large implantation device of about 2 mm. That is, a soft and sticky region of the implantation device, e.g. of a bone pin, may be about 0.1 mm to 1 mm thick, wherein the direction of the thickness is measured in a radial direction of a substantially cylindrical implantation device.

The use of a implantation device which still have a hard and stable core region may make the introducing of the implantation device into the target structure or attaching to the target structure easier and more efficient, since an overall integrity of the implantation device may be maintained.

According to an exemplary embodiment the implantation device is formed as a bone pin. In particular, the bone pin comprises a shaft, and the shaft comprises the peripheral region.

According to another exemplary embodiment of the implantation device the peripheral region comprises a first portion and a second portion, wherein the first portion is adapted to be fixed onto a first bone fragment, and wherein the second portion is adapted to be fixed onto a second bone fragment.

The above described embodiment may enable a fixation of two fragments ends of a target structure, e.g. a bone, to two ends of an implantation device. Thus, the implantation device may form a joining between the two fragments of the bone. In order to possibly improve the connection between the two bone fragments and the implantation device the two bone fragments may be pressed onto the implantation device.

According to another exemplary embodiment of the implantation device the implantation device is formed as a bone plate. In particular, the peripheral region may be formed by or may comprise least one protrusion, wherein the at least one protrusion is adapted to be fixed to a first bone fragment. The peripheral region may be formed by two protrusions, for example, wherein a first one of the protrusions is adapted to be fixed to a first bone fragment, and wherein a second one of the protrusions is adapted to be fixed to a second bone fragment. Preferably, the two protrusions may be formed on one side of the bone plate.

Such protrusions may form a joining element between a bone plate and bone fragments. In particular, one protrusion of the bone plate may be fixed to each bone fragment, so that a plurality of bone fragments may be connected to each other by the bone plate. In order to achieve a possible improvement of the connection between the bone plate and the bone fragments, and thus an improved fixation of the bone fragments with respect to each other, the bone plate may be pressed onto the different bone fragments.

According to another exemplary embodiment of the implantation device the main body is formed by a granule. In particular, the peripheral region may be formed by the surface of the granule and the whole surface is plastified.

Such an implantation device may be in particular suitable to be implemented or attached to smaller target fragments, like small bone fragments. The granule may be formed by a coated granule, wherein the coating corresponds or builds to the plastified peripheral region, i.e. each single granule is surrounded by a plastified region.

In the following, further exemplary embodiments of the method of producing the implantation device will be described. However, these embodiments apply also for the implantation device and for the method for applying the implantation device.

According to an exemplary embodiment of the method for producing the implantation device the dipping is done in such a way that a shape of the implantation device is substantially the same before and after the dipping. In particular, the primary implantation device may be dipped into the plasticizer for a short time span. In case of a bone pin or a granule the dipping may be done in such a way that a diameter of the bone pin or the granule is substantially the same before and after the dipping.

According to an exemplary embodiment a method for applying a bone pin into a target structure comprises forming a hole into the target structure, wherein the hole has a first diameter, and introducing a bone pin according to an exemplary embodiment into the bore, wherein the bone pin has a second diameter which is greater than the first diameter. In particular, the hole may be formed by drilling.

In general, implantation devices according to an exemplary embodiment may be used in different fields of fixation of bone fragments. In particular, resorbable implantation devices, e.g. bone pins, may be used in the field of small fragment fixation of foot, ankle, wrist, elbow and shoulder, resorbable mesh/plate and pins may be used in the field of small fragment fixation of ankle, wrist, and graft containment and hybrid metal and resorbable pins may be used in the field of distal locking, bone anchor, femoral neck fractures, trochaneric fractures, and ex fix pin fixation in osteoporotic bones. In particular, the bone pin may be used for axially stable anchoring of bone plates.

Summarizing, it may be seen as an exemplary aspect of the present invention that a bone pin having a softened outer surface is provided. The technology to produce such a bone pin is based upon the use of a so-called plasticizer, e.g. N-Methyl Pyrolidone (NMP) as a "surface plasticizer" of a bone pin. The idea of this aspect may be to dip a polymer pin, e.g. resorbable or another polymer such as implantable grade polyethylene or nylon, into the plasticizer so that the outer surface area becomes sticky and soft, while the pin core remains solid. In this surfacing process the diameter of the bone pin preferably stays the same. In a next step the surface softened polymer pin may be placed into cancellous bone. Preferably, the diameter of the sticky bone pin is slightly greater than that of a drilled bone hole so that the sticky material may fill the bone pores. The contact of the NMP with blood may chemically reverses the process since NMP hardens when it comes into contact with blood. After the plasticizer has leached into the circumferentially surrounding bone, the "core polymer" material may be firmly fixed in the bone hole. Since, the bone pin comprises a softened outer layer which becomes solid again due to the interaction with body fluids no sonic fusion may be required achieve a stable connection between the bone pin and the bone. Thus, it may be possible to reduce the sound and thermal impact on bone and tissue.

These and other aspects of the present invention will become apparent from and elucidated with reference to the embodiment described hereinafter.

BRIEF DESCRIPTION OF THE DRAWINGS

An exemplary embodiment of the present invention will be described in the following, with reference to the following drawings.

FIG. 1A shows a schematic illustration of a bone pin according to an exemplary embodiment before surfacing;

FIG. 1B shows a schematic illustration of the bone pin of FIG. 1A after surfacing;

DETAILED DESCRIPTION OF AN EXEMPLARY EMBODIMENT

Figure 2A:
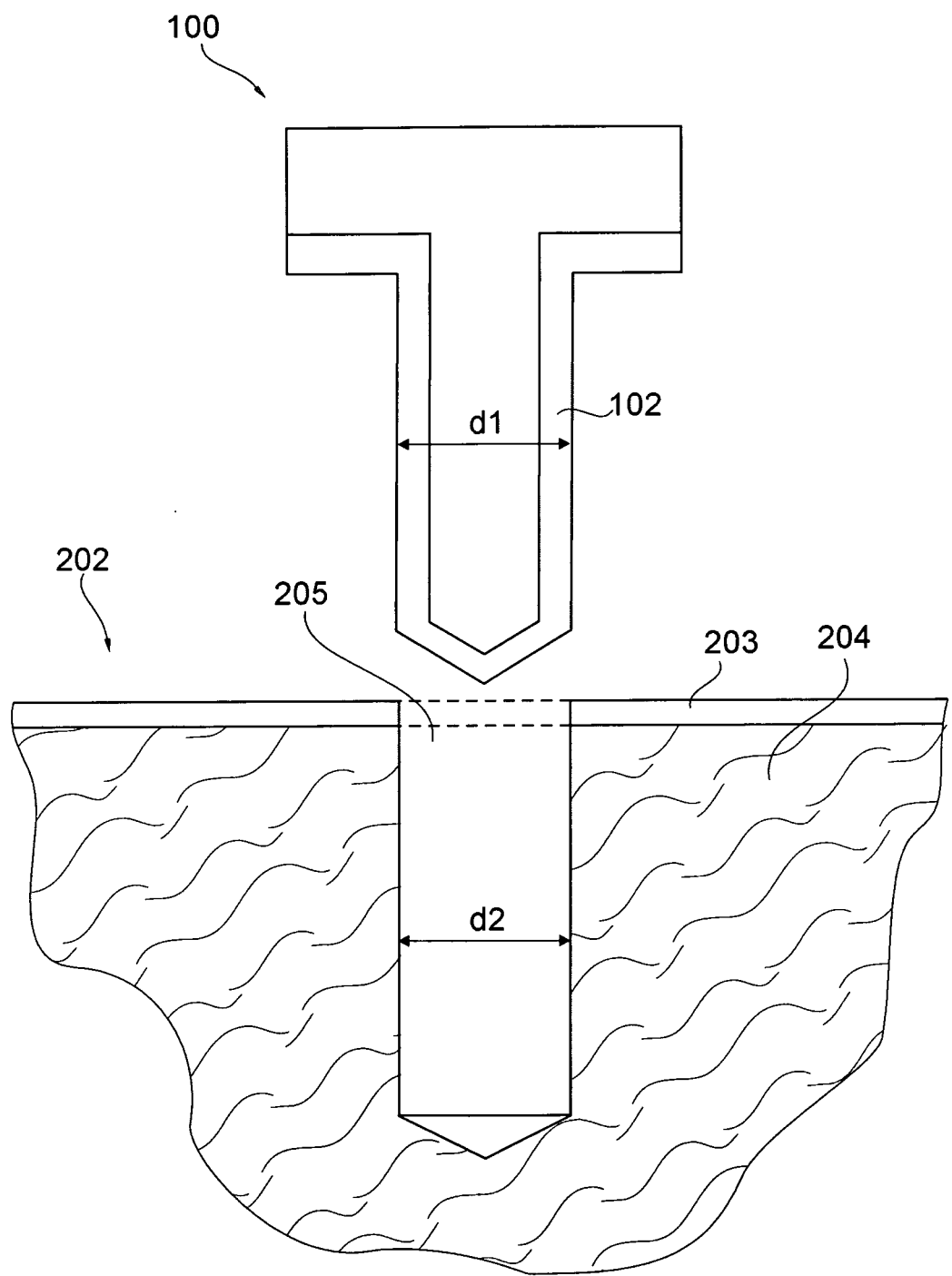
FIGS. 2A and 2B schematically show a process of inserting the bone pin according to an exemplary embodiment.

The illustration in the drawings is schematically. In different drawings, similar or identical elements are provided with similar or identical reference signs.

FIG. 1A shows a schematic illustration of a bone pin according to an exemplary embodiment before surfacing. The bone pin 100 comprises a shaft 101, which is substantially cylindrical in shape. The bone pin is made of polymer material which is preferably bioabsorbable. The schematically shown bone pin 100 has a planar tip, while generally the bone bin has a conical tip.

FIG. 1B shows a schematic illustration of the bone pin 100 of FIG. 1A after surfacing. That is, after the bone pin 100 has been dipped into a plasticizer. Due to this dipping into the plasticizer, e.g. N-Methyl Pyrolidone, the surface becomes soft and plastic, i.e. formable. However, only the outer surface of the bone pin becomes soft, while a core region of the bone pin maintains solid. At a result of this dipping a soft and sticky layer 102 is formed at the outer surface of the bone pin 100 but the total diameter of the shaft remains substantially constant. That is, no additional layer is formed on the primary shaft, but the plasticizer penetrates the bone pin and softens the solid polymer material of the primary bone pin.

FIG. 2 schematically shows a process of inserting the bone pin according to an exemplary embodiment into a bone. In FIG. 2A a bone pin 100 having a softened layer 102 is shown. The diameter of the bone pin 100 is labelled $d_1$ in FIG. 2A. Further, a bone 202 is shown which comprises a cortical bone shell, which is labelled 203, while the cancellous bone is labelled 204. Before inserting the bone pin 100 into the bone 202 a hole 205 is drilled into the bone, wherein the hole has a diameter $d_2$. Preferably, the diameter $d_2$ of the hole is slightly smaller than the diameter $d_1$ of the bone pin.

Figure 2B:
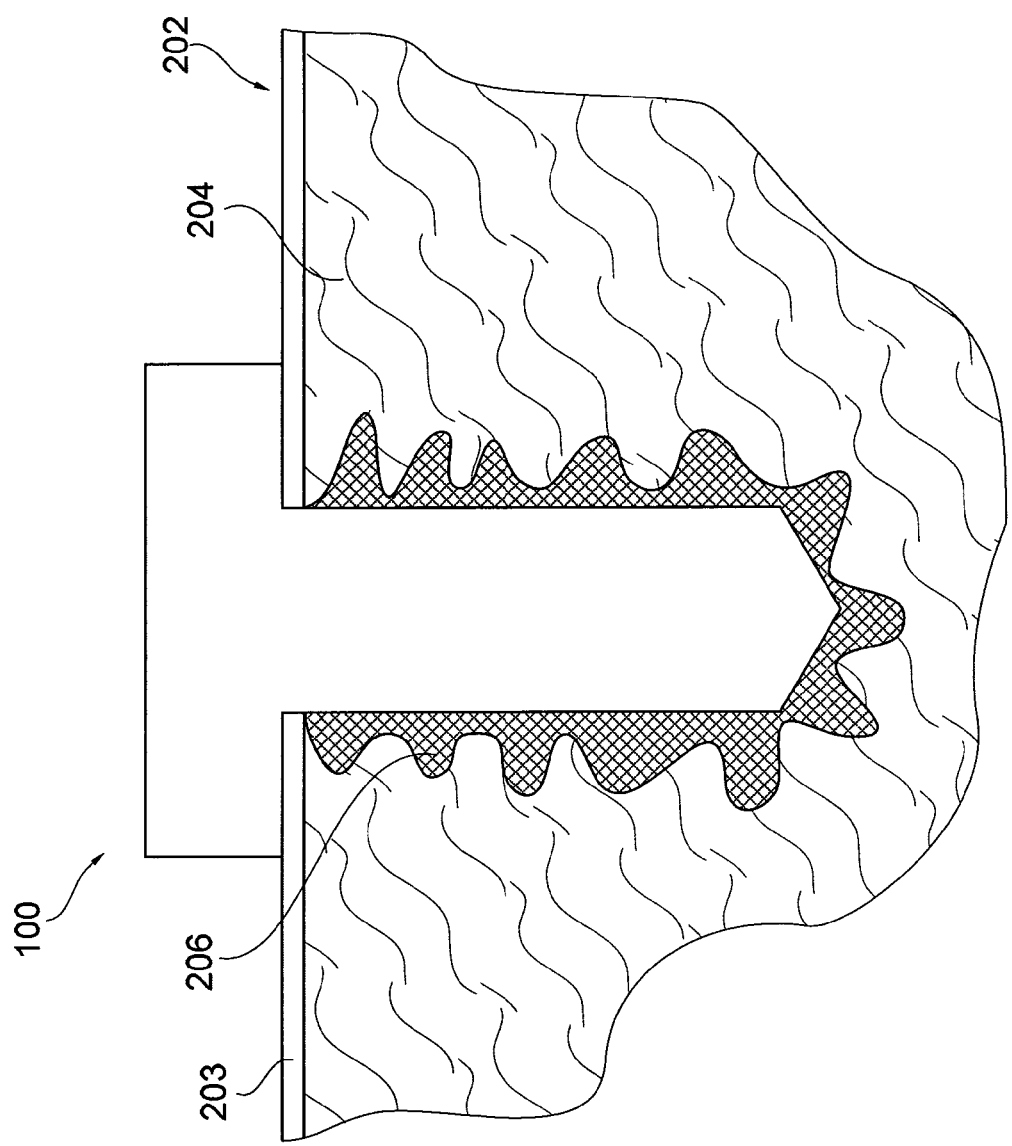

FIG. 2B schematically shows the situation after the bone pin 100 is inserted into the bone 202. The insertion is done by simply pushing the bone pin into the hole 205. In the pushing process the softened outer surface layer 102 interacts with pores of the bone material in a digitate manner, i.e. protrusions are formed looking like fingers by pressing the soft layer into the bone pores, which protrusions engages into the pores of the bone. After the bone pin is pushed into the hole 205, the interaction of the softened outer surface and body fluids reverses softening process. The plasticizer leaches out of the polymeric material such that the material of the bone pin becomes solid again. In this way a stable fixation of the bone pin into the bone may be achieved.

Figure 3:
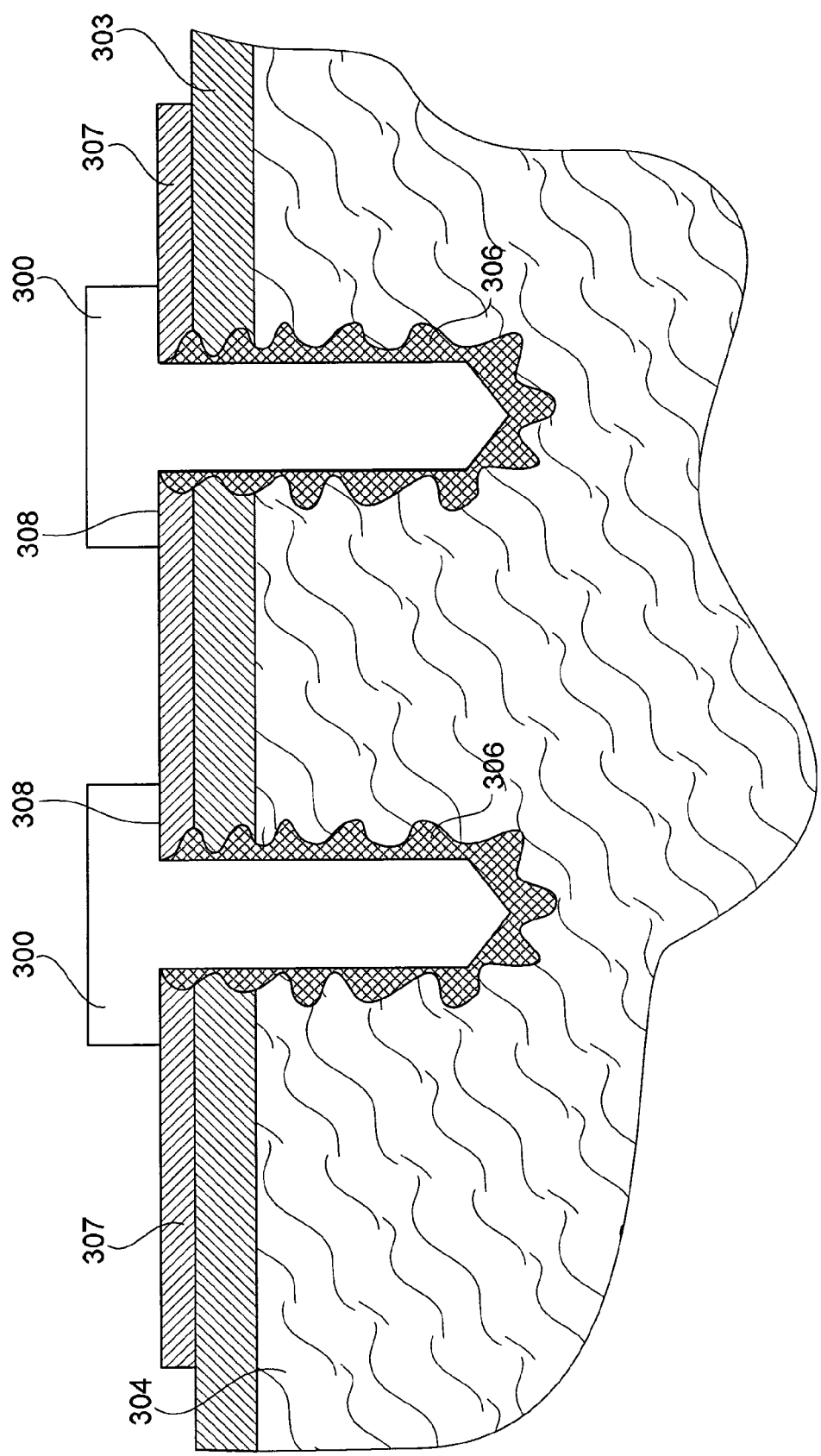
FIG. 3 schematically shows a bone plate which is fixed by bone pins according to an exemplary embodiment.

FIG. 3 schematically shows a bone plate 307 which is fixed by bone pins 300 according to an exemplary embodiment. FIG. 3 schematically shows two bone pins 300 which are inserted through holes in the polymer bone plate, i.e. a bone plate comprising polymer material, into a bone 304 comprising a cortical bone shell, which is labelled 303, while the cancellous bone is labelled 304. As described in connection with the embodiment shown in FIGS. 2A and 2B protrusions 306 are formed from the softened outer surface of the bone pins which protrusions engage with pores in the bone 304. However, due to the using of a polymer bone plate 307 also a stable connection between the bone pins 300 and the polymer bone plate 307 is achieved, which stable connection is schematically shown as protrusions or connections 308 in FIG. 3. These connections 308 are formed by initially leaching of the plasticizer into the polymer of the bone plate which leaching softens the bone plate as well so that a connecting of the polymeric material of the bone pin and the polymeric material of the bone plate is possible. Afterwards the plasticizer is leached out of the bone pin and the bone plate by body fluids so that the connection between bone pin and bone plate becomes solid and stable. Thus, leading to a axially stable construct of bone pin and bone plate.

Figure 4B:
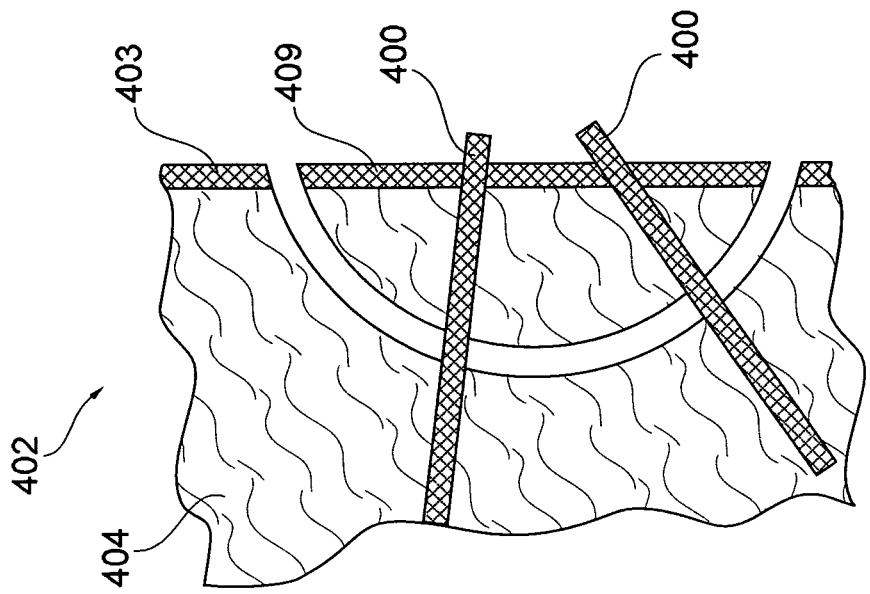
FIG. 4B schematically shows the bone of FIG. 4A after the bone fragment is fixed to the bone.
Figure 4A:
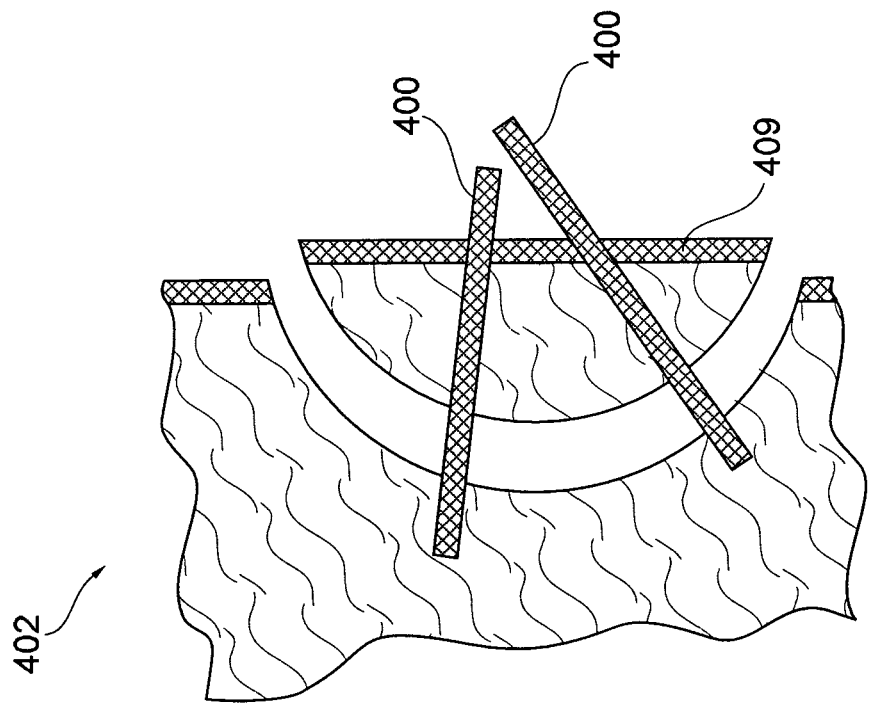
FIG. 4A schematically shows a bone and a bone fragment before the bone fragment is fixed to the bone.

FIG. 4A schematically shows a bone 402 and a bone fragment 409 which is torn off the bone 402 before the bone fragment 409 is fixed to the bone. For fixing two bone pins 400 according to an exemplary embodiment of the invention may be used. In FIG. 4A not the bone pins itself are shown but only the path along which the bone pins are inserted. FIG. 4B schematically shows the bone 402 of FIG. 4A in an enlarged view after the bone fragment 409 is fixed to the bone. In FIG. 4B the cancellous bone is labelled 404 while the cortical bone is labelled 403. The bone pins 400 are inserted through hole drilled into the bone fragment 409 and the bone 402 so that the bone fragment 409 is steadily fixed to the bone 402.

Figure 5:
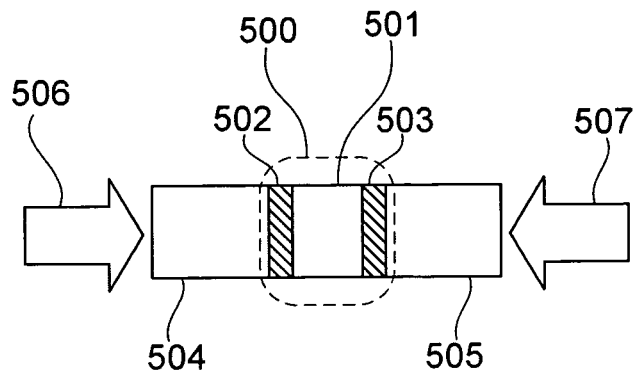
FIG. 5 schematically shows an implantation device according to an exemplary embodiment.

FIG. 5 schematically shows an implantation device according to an exemplary embodiment. The implantation device 500 comprises a peripheral region which is plastified and a core region 501 which is solid, i.e. not plastified. The plastified region is schematically depicted as a first region 502 and a second region 503. The first region 502 may be arranged at one end of the implantation device 500, while the second region 503 is arranged at an opposite end of the implantation device 500. The implantation device 500 is arranged between two bone fragments, wherein the first region 502 is fixed to a first bone fragment 504 and the second region 503 is fixed to a second bone fragment 505. Thus, the bone fragments ends are connected to the plastified regions of the implantation device, so that they stick to the implantation device. In order to strengthen the connection a force may be applied to the bone fragments in such a direction that the ends of the bone fragments are securely pressed against the plastified peripheral regions, which may be also called sticky regions, of the implantation device. The force is schematically indicated in FIG. 5 by the arrows 506 and 507.

Figure 6:
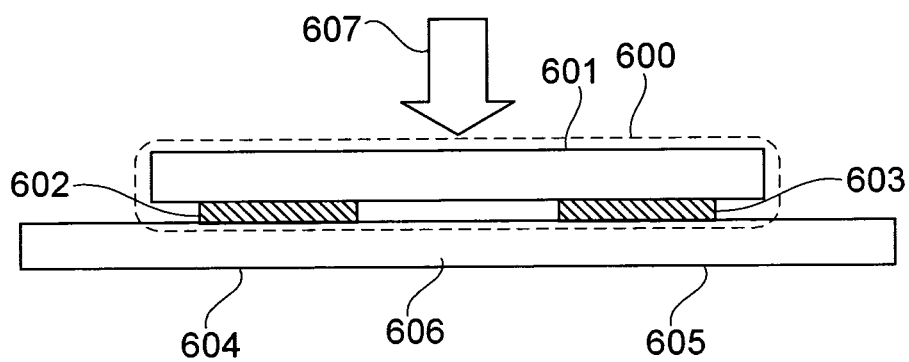
FIG. 6 schematically shows another implantation device according to another exemplary embodiment.

FIG. 6 schematically shows another implantation device according to another exemplary embodiment. The implantation device 600 is formed as a bone plate and comprises a peripheral region which is plastified and a solid region 601 which is not plastified. According to the embodiment shown in FIG. 6 the peripheral region is formed by a first protrusion 602 and a second protrusion 603, which both are plastified. The two protrusions are formed on one side of the bone plate 600. The bone plate 600 may be arranged on a fractured bone in order to fixate two bone fragments with respect to each other. In particular, the first protrusion 602 may be arranged or attached to a first bone fragment 604, while the second protrusion 603 is attached to a second bone fragment 605. A fracture of the corresponding bone is indicated in FIG. 6 by a crack 606. In order to strengthen the connection a force may be applied to the bone plate in such a direction that the protrusions of the bone plate are securely pressed against the bone fragments. The force is schematically indicated in FIG. 6 by the arrow 607.

Figure 7:
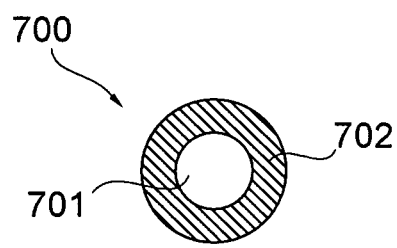
FIG. 7 schematically shows another implantation device according to another exemplary embodiment.

FIG. 7 schematically shows another implantation device according to another exemplary embodiment. The implantation device 700 is formed as a granule and comprises a peripheral region 702 which is plastified and a solid region 701 which is not plastified. The granule may be in particular formed as a small sphere, ellipsoid, or cuboid, i.e. as a small volume which is suitable to be filled into a small hole, crack, or the like. Dependent on the size of the hole or crack several granules 700 may be used in order to fixate the fragment of a bone.

Summarizing it may be seen as one exemplary embodiment of the present invention to provide a bone pin having a polymeric shaft comprising a peripheral region which is softened by a plasticizer. That is, the bone pin comprises a soft and sticky outer surface. When such a bone pin is pressed or pushed into a drilled hole in a bone having a slightly smaller diameter than the bone pin itself, the softened layer of the bone pin may engage with bone pores. After insertion is completed the softener may leach out of the softened material so that this material will solidify again possibly leading to a stable connection between the bone pin and the bone.

It should be noted that the term "comprising" does not exclude other elements or steps and the "a" or "one" does not exclude a plurality. Also elements described in association with different embodiments and aspects may be combined. It should also be noted that reference signs in the claims shall not be construed as limiting the scope of the claims.

The invention claimed is:

1. An implantation device for fixating a bone, the implantation device comprising:
    a bone pin comprising a main body,
    wherein the main body is formed with a polymeric core region and an outer polymeric peripheral region, the outer peripheral region surrounding the core region having a thickness between 0.1 mm and 1.0 mm;
    wherein the main body polymeric core region consists entirely of a polymeric material free of a plasticizer; and
    wherein the polymeric peripheral region is made of the polymeric material and a plasticizer, so that the peripheral region is soft and the core region is solid, whereby the peripheral region is deformable when implanted into the bone and after implantation the plasticizer in the peripheral region reacts with body fluid so that it leaches out of the peripheral region of the main implant body;
    wherein the bone pin comprises a head and a shaft; and
    wherein the shaft comprises the core and the peripheral region, and the head includes a surface extending outwardly from the shaft in a direction transverse to the shaft, the surface having the peripheral region.

2. The implantation device according to claim 1, wherein the peripheral region is adapted to be fixed to a bone.

3. The implantation device according to claim 1, wherein the polymeric material is bioabsorbable.

4. The implantation device according to claim 1, wherein the polymeric material is selected from the group consisting of:
  polyethylene, and nylon.

5. The implantation device according to claim 1, wherein the plasticizer is N-Methyl Pyrrolidone.

6. The implantation device according to claim 1, wherein the peripheral region comprises a first portion and a second portion;
  wherein the first portion is adapted to be fixed onto a first bone fragment; and
  wherein the second portion is adapted to be fixed onto a second bone fragment.

7. The implantation device according to claim 1, wherein the implantation device further comprises a bone plate.

8. The implantation device according to claim 7,
  wherein the peripheral region is formed by least one protrusion, wherein the at least one protrusion is adapted to be fixed to a first bone fragment.

9. The implantation device according to claim 7 wherein the peripheral region is formed by two protrusions,
  wherein a first one of the protrusions is adapted to be fixed to a first bone fragment; and
  wherein a second one of the protrusions is adapted to be fixed to a second bone fragment.

10. The implantation device according to claim 9, wherein the two protrusions are formed on one side of the bone plate.

11. The implantation device according to claim 1, wherein the main body is formed from granules.

12. The implantation device according to claim 11, wherein the whole peripheral region is formed by the surface of the granules; and
  wherein the whole surface of the peripheral region is plastified.

13. An implantation device for fixing a base, the implantation device comprising:
  a bone pin comprising a body having a core region made exclusively of a polymeric material free of platicizers, the polymeric material is selected from the group consisting of a copolymer comprising between 50% and 90% poly-L-lactide and between 10% and 50% poly D, L-lactide, polyesters, polyorthoesters, polylactides (PLA), polyglycolides (PGA), polycaprolactones, polyhydroxybutyrates, polyhydroxyvalerates, pseudopolyamino acids, polyamides and polyanhydrides; oligomers of glycolic acid and/or lactic acid and their derivatives with alcohols and/or carbonic acids; polylactide-glycerate; polyglycolide-co-glycerate; polyamides; oligomers of hydroxycarbonic acids; poly(ortho)esters; and cross-linked cellulosic polymers (e.g., caroboxymethyl cellulose); glycolide/lactide copolymers (PGA/PLA), glycolide/trimethylene carbonate copolymers (PGA/TMC), poly-.beta.-hydroxybutyric acid (PHBA), poly-.beta.-hydroxypropionic acid (PHPA), poly-.beta.-hydroxyvaleric acid (PHVA), PHBA/PHVA copolymers, poly-p-dioxanone (PDS), poly-1,4-dioxanon-2,5-dione, polyesteramides (PEA), poly-.epsilon.-caprolactones, poly-.delta.-valerolactone, poly-carbonate, polyesters of oxalic acid, glycolic esters, dihydropyranes, polyethylene, polyethylene glycols, polyesteramides, polyorthoesters, polydioxanones (PDS), polyacetals, polyketals, polycarbonates, polyorthocarbonate, polyphosphazenes, polyhydroxybutyrates, polyhydroxyvalerates, polyalkylene oxalates, polyalkylene succinates, poly(malic acid), poly(amino acids), poly methyl vinyl ether), chitin, chitosan, an implantable grade nylon and a combination thereof, the core region surrounded by a peripheral region made of the polymeric material and a plasticizer; and
  the peripheral region made of the polymeric material and a plasticizer are selected from the group consisting of citrates, phthalates, glycol ethers, N-methylpyrrolidone, 2 pyrrolidone, propylene glycol, glycerol, glyceryl dioleate, ethyl oleate, benzylbenzoate, glycofurol, sorbitol, sucrose acetate isobutyrate, butyryltri-n-hexyl-citrate, acetyltri-n-hexyl citrate, sebacates, dipropylene glycol methyl ether acetate (DPM acetate), propylene carbonate, propylene glycol methyl ether acetate (DPM acetate), propylene carbonate, propylene glycol laurate, propylene glycol captylate/caprate, caprylic/capric triglyceride, gamma butyrolactone, polyethylene glycols (PEGs), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di and tri stearate, glyceryl palmitostearate, glyceryl triacetate, ethanol, acetone, acetic acid, ethyl acetate, ethyl lactate, methyl acetate, methyl ethyl ketone, dimethylformamide, dimethyl sulfoxide, dimethyl sulfone, tetrahydrofuran, caprolactam, decylmethylsulfoxide, oleic acid, propylene carbonate, N,N-diethyl-m-toluamide, 1-dodecylazacyclolheptan-2-one and a combination thereof, whereby the peripheral region is deformable when implanted into the bone and after implantation the plasticizer in the peripheral region reacts with body fluid so that it leaches out of the peripheral region of the main implant body;
  wherein the bone pin comprises a head and a shaft; and
  wherein the shaft comprises the core and the peripheral region, and the head includes a surface extending outwardly from the shaft in a direction transverse to the shaft, the surface having the peripheral region.

14. An implantation device for fixating a bone, the implantation device comprising:
  a bone pin comprising a main body comprising a bioresorbable polymer
  wherein the main body is formed with a solid core region made exclusively of the bioresorbable polymer free of a plasticizer and a peripheral region, the peripheral region having a thickness between 0.1 mm and 1.0 mm;
  wherein the peripheral region consists of the bioresorbable polymer with N-Methyl Pyrolidone therein, so that the peripheral region is softer than the solid core region, with a shape of the implantation device being substantially the same with or without the N-Methyl-Pyrolidone in the peripheral region of the bioresorbable polymer whereby the peripheral region is deformable when implanted into the bone and after implantation the plasticizer in the peripheral region reacts with body fluid so that it leaches out of the peripheral region of the main implant body;
  wherein the bone pin comprises a head and a shaft; and
  wherein the shaft comprises the core and the peripheral region, and the head includes a surface extending outwardly from the shaft in a direction transverse to the shaft, the surface having the peripheral region.

* * * * *